US00PP27536P3

(12) United States Plant Patent
Hanna et al.

(10) Patent No.: US PP27,536 P3
(45) Date of Patent: Jan. 10, 2017

(54) PERENNIAL PEANUT 'PP-1'

(50) Latin Name: *Arachis glabrata*
Varietal Denomination: PP-1

(71) Applicant: University of Georgia Research Foundation, Inc., Athens, GA (US)

(72) Inventors: Wayne W. Hanna, Chula, GA (US); Brian M. Schwartz, Tifton, GA (US); Ann Rachel Soffes Blount, Quincy, FL (US)

(73) Assignee: University of Georgia Research Foundation, Inc., Athens, GA (US)

( * ) Notice: Subject to any disclaimer, the term of this patent is extended or adjusted under 35 U.S.C. 154(b) by 358 days.

(21) Appl. No.: 14/120,105

(22) Filed: Apr. 25, 2014

(65) Prior Publication Data

US 2015/0313055 P1 Oct. 29, 2015

(51) Int. Cl.
*A01H 5/08* (2006.01)

(52) U.S. Cl.
USPC ..... Plt./258

(58) Field of Classification Search
USPC ..... Plt./258, 152
CPC ..... A01H 5/02; A01H 5/0825; A01H 5/10
See application file for complete search history.

*Primary Examiner* — Kent L Bell
(74) *Attorney, Agent, or Firm* — Klarquist Sparkman, LLP

(57) ABSTRACT

The new cultivar of *Arachis glabrata* 'PP-1' is provided. The new and distinct variety has high ornamental value, abundance of yellow orange flowers, dark green leaf color, and low maintenance after establishment. The asexually reproduced cultivar is reliably propagated vegetatively.

2 Drawing Sheets

Latin name of the genus and species of the plant claimed: 'PP-1' is a vegetatively propagated ornamental perennial peanut cultivar of the genus and species *Arachis glabrata.*

Variety denomination: The new *Arachis glabrata* claimed is of the cultivar denominated 'PP-1'.

BACKGROUND OF THE INVENTION

The present invention relates to a new and distinct cultivar of *Arachis glabrata* herein referred to as 'PP-1'.

The new *Arachis glabrata* is a product of a planned research and evaluation program conducted by the Inventors in Tifton, Ga. The objective of the *Arachis glabrata* research program is to create new plant cultivars with improved commercial qualities. This cultivar is commercially important for its superior ornamental value. These and other qualities are enumerated herein.

Pedigree and history: Annual reports by J. L. Stephens, a research agronomist show that Mr. Stephens introduced 12 wild *Arachis* species and evaluated them in test plots at Tifton, Ga. from 1952 to 1954. One accession was designated as *A. glabrata*, three accessions were designated as *A. marginata*, and the remaining accessions were designated as unknown 'sp.' with a number. Observations indicated broad morphological variation within the *A. glabrata* species, therefore difficulty in establishing species identity without expert assistance. Mr. Stephens wrote in his 1953 annual report that three accessions, *Arachis* sp. 172223, *Arachis* sp. 172224, and *Arachis* sp. DETP 6519 (all unpatented) showed potential for cattle pastures and were vegetatively planted in two-acre pastures in 1954. However, the perennial peanut research was not mentioned in Mr. Stephens' annual reports after 1954; probably due to establishment problems due to vegetative propagation.

'PP-1' is a vigorous *Arachis glabrata* plant growing on its own for over 50 years in Tifton, Ga. on the eastern edge of the test plots used in 1952 to 1954 to test perennial peanut introductions. 'PP-1' probably arose from either an outcross among the *A. glabrata* accessions being evaluated or a superior genetic recombination from an *A. glabrata* introduction growing in the 1952 to 1954 plots at Tifton, Ga. *A. glabrata* flowers profusely and will set occasional seeds. It was discovered by the inventors growing in a natural uniform stand 7 m wide and 123 m long on the eastern edge of the 1952 to 1954 research plots. Growth or spread of the 'PP-1' stand has been limited on the east side by herbicides sprayed along U.S. Route 41 and limited on the west side by cultivation and herbicides. Pictures of 'PP-1' were sent to Dr. Charles Simpson to help with identification. Dr. Simpson sent the inventor a sample of the *Arachis glabrata* 'A42' variety (unpatented) which was then compared with 'PP-1'. 'A42' has wider leaves (Table 8) and more leaf area per leaf (Table 10) than 'PP-1'.

A fourteen amplified fragment length polymorphism AFLP study on "Genetic Variability of Cultivated Rhizome Peanut" by Maas, Anderson and Quesenberry [Crop Science 50:1908-1914 (2010)] revealed that 'PP-1' is most related to 'Florigraze' (unpatented), a broad leaf and tall perennial peanut type plant. 'PP-1' is referred to as UGA Experimental in the Maas et al., study; the study also included released or soon to be released cultivars and accessions with commercial cultivar potential (the study did not include all of the perennial peanut germplasm in GRIN). Morphologically, 'PP-1' is most similar to the germoplasm perennial peanut plant 'Brooksville 68' (unpatented) commonly referred to as 'Pointed Leaf' for which planting stock was not available when we established the 2006 test at Tifton. 'PP-1' produces infrequent viable seed. We looked at 40 plants produced from seed of 'PP-1' and found that a wide range of morphological types were produced, none with the vigor and persistence of 'PP-1'.

Asexual reproduction of the new *A. glabrata* 'PP-1' by vegetative propagation from single rhizome sections in a controlled environment in Tifton, Ga. since 2005, has shown that the unique features of this new *A. glabrata* cultivar are stable and reproduced true to type in successive generations.

SUMMARY OF THE INVENTION

The following traits have been repeatedly observed and represent the characteristics of the new *A. glabrata* cultivar 'PP-1'. The new cultivar 'PP-1' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been repeatedly observed in Tifton, Ga.; Gainesville and Quincy, Fla. and are determined to be the unique characteristics of the new cultivar 'PP-1':

1. 'PP-1' reaches a height of about 20 cm.
2. 'PP-1' produces an abundance of flowers. Wing petals are Yellow-Orange Group 14D and Stand Petals transition from Orange Group 24C in the center to Yellow-Orange Group 14C toward the margins.
3. 'PP-1' produces a dense dark green canopy.

The new *A. glabrata* cultivar 'PP-1' can be compared to 'Florigraze', 'Pointed Leaf' and 'Ecoturf' (unpatented).

Plants of the new *A. glabrata* cultivar differ from 'Florigraze' in the following characteristics:

1. The new cultivar 'PP-1' produces more flowers than 'Florigraze'.
2. The new cultivar 'PP-1' has a darker green plant color, maintains higher turf quality, is more dense, has narrower leaves, and has lower Pepper Spot ratings than 'Florigraze'.

Plants of the new *A. glabrata* cultivar differ from 'Pointed Leaf' in the following characteristics:

1. The new cultivar 'PP-1' has narrower leaves and less leaflet area than 'Pointed Leaf'.

Plants of the new *A. glabrata* cultivar differ from 'Ecoturf' in the following characteristics:

1. The new cultivar 'PP-1' maintains higher turf quality than 'Ecoturf'.
2. Flower number ratings are significantly higher at most rating dates for 'PP-1' compared to 'Ecoturf'.
3. 'PP-1' has significantly narrower leaves and significantly less total leaflet area then 'Ecoturf'.

The following observations, measurements, and values describe plants grown in Tifton, Ga., Quincy, Fla. and Gainesville, Fla. In Tables 1-18, the least significant difference (LSD) is set at $P \leq 0.05$ probability level. In 2006 we established 'PP-1' in a test at Tifton, Ga. (3.7×3.7 m plots, four replications) with other released or soon-to-be released perennial peanut cultivars. Dr. Kevin Kenworthy provided us planting materials of 'Ecoturf', 'Arblick', 'Florigraze', and 'Arbrook'. Dr. Ann Blount established tests (1.5×3.1 m plots) at Quincy, Fla. (five replications) and at Gainesville, Fla. (four replications) with the same cultivars plus 'Pointed Leaf' at Quincy, Fla. (10 Apr. 2009) and at Gainesville, Fla. (28 Jun. 2010). Dr. Mimi Williams, breeder of 'Pointed Leaf', provided us planting material of this cultivar in 2010. Eight replications of 'Pointed Leaf' and 'PP-1' were established as single plant propagules on 14 Jun. 2011 at Tifton, Ga. Plots at Tifton received 560 kg/ha 5-10-15 preplant and 280 kg/ha 5-10-15 yearly in April after establishment. Plots in Florida did not receive any fertilizer.

'PP-1' is a perennial, vegetatively propagated dark-green narrow-leaf perennial peanut recommended for use as an ornamental in USDA zones 8b and 9. It has survived in a 2006 replicated test at Tifton from 2006 to 2012 (when the test was destroyed). 'PP-1' was in the top statistical group for flower number on 10 of the 13 rating dates during 2008 to 2011 at Tifton (Table 1), in 3 of 5 rating dates at Quincy, Fla. in 2010 and 2011 (Table 11), and in 2 of 5 rating dates at Gainesville, Fla. in 2011 and 2012 (Table 12). 'PP-1' had significantly darker green color than the other cultivars at Tifton in 12 of 13 tests (Table 2). Mature leaf color was classified as Green 144A according to The Royal Horticultural Society color index (5$^{th}$ Edition, 2007). 'PP-1' was in the top statistical group for color in 6 of 7 rating dates in the Florida tests (Table 13).

Height of 'PP-1' was similar to 'Ecoturf' on 5 of 6 measuring dates in three years at Tifton, Ga. (Table 3). At most measuring dates it was shorter than 'Arblick' and 'Arbrook' and taller than 'Florigraze'. At Quincy, Fla., 'PP-1', 'Pointed Leaf', and 'Arblick' were similar in height and shorter than 'Ecoturf', 'Florigraze', and 'Arbrook' (Table 14). 'PP-1' was rated in the top statistical group in four of five tests for turf quality (Table 4).

In the establishment year (2006) at Tifton, Ga., 'PP-1' and 'Ecoturf' were slower to establish than the other cultivars (Table 5). However, in subsequent years, 'PP-1' was in the top statistical group for maintaining dense ground cover. Canopy density at Tifton, Ga. (Table 6) was similar for 'PP-1', 'Ecoturf', and 'Arblick' and higher than 'Florigraze' and 'Arbrook' at most rating dates. Canopy density at Quincy, Fla. (Table 15) was similar to 'Pointed Leaf', 'Arblick', and 'Florigraze' at early and mid-season dates, but had less density than the other cultivars, except 'Pointed Leaf' in October due to pepper spot disease (*Leptosphaerulina crassiasca*).

Spring green-up at Gainesville, Fla. was similar for all cultivars, except for 'Florigraze' which showed a slower green-up (Table 16). 'PP-1' showed better freeze tolerance than 'Ecoturf' and 'Arblick' at Gainesville, Fla. and all of the cultivars tested at Quincy, Fla. (Table 16).

At Tifton, Ga., 'PP-1' had low Pepper Spot ratings at October and November rating dates (Table 7). The disease rating was higher at a December date in 2009, but less than the disease on 'Florigraze' and 'Arbrook'. Pepper spot ratings in October were higher for 'PP-1' (and similar to 'Pointed Leaf') at Quincy, Fla. than at Tifton, Ga. (Table 17). Leaf scorch caused by the same organism as pepper spot was higher for 'PP-1' and 'Pointed Leaf' at Gainesville, Fla. than for the other cultivars in the test. Note: the higher disease ratings on 'PP-1' and 'Pointed Leaf' in the Florida tests and in the Tifton test in December 2009 are probably due to fertility—mainly potassium. On 7 Oct. 2012, the 'PP-1' growing in the original collection area next to U.S. Route 41 showed high pepper spot infection while the adjacent fertilized 14 Jun. 2011 test and a Foundation planting showed no disease symptoms. Similar leaf spot symptoms are observed on bermudagrass (*Cynodon dactylon*) in the fall due to the soil being depleted of potassium. No peanut stunt virus (*Cucumovirus*) was detected in 'PP-1' growing at Gainesville, Fla. in 2010, 2011 and 2012 (Table 18).

Morphologically, 'PP-1' is most similar to 'Pointed Leaf'. However 'PP-1' has narrower leaves (Table 8) than 'Pointed Leaf', 'A42', and all of the cultivars tested. 'PP-1' and most of the cultivars tested have similar leaf length except 'Arbrook' which has longer leaves (Table 9). 'PP-1' has smaller leaves than all of the other cultivars except for 'Florigraze' on 25 Jul. 2011 at Tifton, Ga. and 'Pointed Leaf' on 21 Aug. 2010 at Quincy, Fla. (Table 10). Additional morphological characteristics are summarized in Table 18.

A number of propagation studies have been conducted using rhizomes as sod (using a peanut inverter to dig the sod) and dug sprigs (using a traditional bermudagrass sprig harvester). Both propagation materials work well, but sprigs are easier to plant and handle. Best establishment takes place when sprigs are planted in furrows (continuous row of rhizomes with average density of 2 to 4 sprigs side by side), covered with 2.5 cm of soil. Rhizomes planted in 1 m wide rows establish in one year. Closer row spacings speed up establishment. A layer of rhizomes with 80% surface coverage planted in 23×46 cm flats establish as a marketable product in 5 to 6 weeks in the greenhouse.

TABLE 1a

Flower number ratings on five *Arachis glabrata* perennial peanut genotypes planted at Tifton, GA on 18 May 2006.

| | Number of Flowers[z] | | | | | |
|---|---|---|---|---|---|---|
| | 2008 | | | 2009 | | |
| Entry | May 1 | Jul. 1 | Sep. 2 | May 11 | Aug. 11 | Sep. 30 |
| 'PP-1' | 5.5 | 1.3 | 5.8 | 8.7 | 3.5 | 2.0 |
| 'Ecoturf' | 3.0 | 1.8 | 2.5 | 3.0 | 2.2 | 1.2 |
| 'Arblick' | 2.0 | 2.0 | 2.0 | 2.0 | 2.0 | 1.2 |
| 'Florigraze' | 2.3 | 2.0 | 2.0 | 2.5 | 2.0 | 1.7 |
| 'Arbrook' | 1.5 | 2.0 | 1.3 | 2.7 | 1.5 | 1.0 |
| LSD-5% | 0.8 | 0.6 | 0.5 | 0.8 | 0.9 | 0.5 |

[z]1 = no flowers, 2 = less than 20% coverage, 3 = 20 to 30% coverage, 4 = 30 to 40% coverage, 5 = 40 to 50% coverage, 6 = 50 to 60% coverage, 7 = 60 to 70% coverage, 8 = 70 to 80% coverage, 9 = greater than 80% coverage.

TABLE 1b

Flower number ratings on five *Arachis glabrata* perennial peanut genotypes planted at Tifton, GA on 18 May 2006.

| | Number of Flowers[z] | | | | | | |
|---|---|---|---|---|---|---|---|
| | 2010 | | | 2011 | | | |
| Entry | May 15 | Sep. 1 | Sep. 29 | Jan. 20 | Apr. 19 | Apr. 25 | Jul. 27 |
| 'PP-1' | 7.0 | 5.5 | 5.0 | 2.0 | 2.7 | 6.5 | 7.2 |
| 'Ecoturf' | 4.2 | 3.0 | 2.7 | 2.7 | 2.0 | 2.0 | 3.5 |
| 'Arblick' | 4.0 | 4.0 | 2.5 | 2.7 | 1.7 | 2.2 | 2.7 |
| 'Florigraze' | 3.2 | 3.7 | 2.0 | 3.0 | 2.0 | 1.7 | 4.5 |
| 'Arbrook' | 2.0 | 1.7 | 1.0 | 2.2 | 1.5 | 2.0 | 2.0 |
| LSD-5% | 1.1 | 1.5 | 0.7 | NS | 1.0 | 1.7 | 1.1 |

[z]1 = no flowers, 2 = less than 20% coverage, 3 = 20 to 30% coverage, 4 = 30 to 40% coverage, 5 = 40 to 50% coverage, 6 = 50 to 60% coverage, 7 = 60 to 70% coverage, 8 = 70 to 80% coverage, 9 = greater than 80% coverage.

TABLE 2a

Plant color ratings on five *Arachis glabrata* perennial peanut genotypes planted at Tifton, GA 18 May 2006.

| | Color[z] | | | | |
|---|---|---|---|---|---|
| | 2008 | | 2009 | | |
| Entry | 2 May | 7 Oct. | 11 Aug. | 30 Sep. | 16 Dec. |
| 'PP-1' | 7.0 | 8.0 | 8.0 | 9.0 | 9.0 |
| 'Ecoturf' | 6.0 | 6.0 | 5.5 | 6.2 | 6.7 |
| 'Arblick' | 7.0 | 7.0 | 6.0 | 7.2 | 8.0 |
| 'Florigraze' | 4.0 | 4.0 | 4.2 | 4.7 | 4.5 |

TABLE 2a-continued

Plant color ratings on five *Arachis glabrata* perennial peanut genotypes planted at Tifton, GA 18 May 2006.

| | Color[z] | | | | |
|---|---|---|---|---|---|
| | 2008 | | 2009 | | |
| Entry | 2 May | 7 Oct. | 11 Aug. | 30 Sep. | 16 Dec. |
| 'Arbrook' | 8.0 | 7.0 | 4.2 | 5.7 | 5.5 |
| LSD-5% | 1.0 | 1.0 | 0.7 | 0.5 | 1.0 |

[z]Color ratings are: 1 = yellow, 9 = dark green

TABLE 2b

Plant color ratings on five *Arachis glabrata* perennial peanut genotypes planted at Tifton, GA 18 May 2006.

| | Color[z] | | | | | | | |
|---|---|---|---|---|---|---|---|---|
| | 2010 | | | | | 2011 | | |
| Entry | April | Aug. 3 | Sep. 1 | Sep. 29 | Nov. 19 | Apr. 19 | Jun. 20 | Jul. 27 |
| 'PP-1' | 9.0 | 9.0 | 9.0 | 9.0 | 8.0 | 9.0 | 9.0 | 9.0 |
| 'Ecoturf' | 7.7 | 6.5 | 7.5 | 7.0 | 5.0 | 7.5 | 7.5 | 7.2 |
| 'Arblick' | 7.7 | 7.7 | 8.0 | 9.0 | 6.5 | 8.0 | 7.7 | 8.0 |
| 'Florigraze' | 6.2 | 4.0 | 6.2 | 5.5 | 3.5 | 6.2 | 6.5 | 6.0 |
| 'Arbrook' | 8.0 | 6.2 | 7.7 | 7.2 | 5.2 | 7.5 | 7.2 | 7.0 |
| LSD-5% | 0.5 | 0.5 | 0.7 | 0.8 | 0.7 | 0.5 | 0.8 | 0.7 |

[z]Color ratings are: 1 = yellow, 9 = dark green

TABLE 3

Height of live *Arachis glabrata* perennial peanut genotypes planted at Tifton, GA on 18 May 2006.

| | Height (cm)[z] | | | | | |
|---|---|---|---|---|---|---|
| | 2008 | | | 2009 | 2011 | |
| Entry | May 2 | Jun. 2 | Jul. 1 | Oct. 15 | Apr. 19 | Jul. 27 |
| 'PP-1' | 6.0 | 8.0 | 10.0 | 18.5 | 13.0 | 19.5 |
| 'Ecoturf' | 6.0 | 8.0 | 11.0 | 20.5 | 5.7 | 18.7 |
| 'Arblick' | 8.0 | 9.0 | 13.0 | 30.0 | 10.2 | 25.0 |
| 'Florigraze' | 4.0 | 7.0 | 14.0 | 19.0 | 4.5 | 16.7 |
| 'Arbrook' | 14.0 | 16.0 | 17.0 | 27.0 | 14.0 | 23.7 |
| LSD-5% | 2.0 | 1.0 | 2.0 | 3.1 | 2.3 | 4.7 |

[z]Plant height measured from ground level to top of plant canopy.

TABLE 4

Turf quality of five *Arachis glabrata* perennial peanut genotypes planted at Tifton, GA on 18 May 2006.

| | Turf Quality[z] 2008 | | | | |
|---|---|---|---|---|---|
| Entry | Jun. 2 | Jul. 7 | Aug. 1 | Sep. 2 | Oct. 7 |
| 'PP-1' | 6.5 | 9.0 | 8.0 | 9.0 | 6.8 |
| 'Ecoturf' | 6.0 | 7.0 | 7.8 | 7.3 | 5.8 |
| 'Arblick' | 7.8 | 7.8 | 8.0 | 8.0 | 6.8 |
| 'Florigraze' | 3.5 | 5.5 | 4.5 | 4.3 | 4.8 |
| 'Arbrook' | 4.0 | 3.8 | 5.3 | 2.5 | 6.3 |
| LSD-5% | 1.1 | 0.9 | 0.7 | 1.0 | 0.8 |

[z]Visual turf quality (based on color, density, and texture) rating on scale of 1 to 9 with 1 = poor and 9 = excellent. A rating of 6 is considered acceptable turf quality.

TABLE 5

Percent ground cover on five *Arachis glabrata* perennial peanut genotypes planted at Tifton, GA on 18 May 2006.

| | % Cover[z] | | | | |
|---|---|---|---|---|---|
| | 2006 | 2009 | 2010 | 2011 | |
| Entry | Oct. 20 | Apr. 9 | Apr. 12 | Apr. 19 | Jan. 20 |
| 'PP-1' | 42.0 | 97.5 | 100.0 | 9.0 | 9.0 |
| 'Ecoturf' | 57.0 | 70.0 | 95.0 | 5.2 | 7.0 |
| 'Arblick' | 75.0 | 87.5 | 97.0 | 6.7 | 8.5 |
| 'Florigraze' | 77.0 | 10.0 | 77.0 | 2.0 | 5.2 |
| 'Arbrook' | 72.0 | 35.0 | 57.0 | 4.0 | 7.0 |
| LSD-5% | 17.0 | 11.7 | 11.0 | 1.6 | 2.1 |

[z]1 = less than 20% canopy coverage, 2 = 20 to 30% canopy coverage, 3 = 30 to 40% canopy coverage, 4 = 40 to 50% canopy coverage, 5 = 50 to 60% canopy coverage, 6 = 60 to 70% canopy coverage, 7 = 70 to 80% canopy coverage, 8 = 80 to 90% canopy coverage, 9 = 100% canopy coverage,

TABLE 6

Canopy density ratings on five *Arachis glabrata* perennial peanut genotypes planted at Tifton, GA 18 May 2006.

| | Density[z] | | | | | | |
|---|---|---|---|---|---|---|---|
| | 2008 | 2009 | 2010 | | | | 2011 |
| Entry | Oct. 7 | Oct. 15 | Aug. 3 | Sep. 1 | Sep. 29 | Nov. 29 | Jul. 27 |
| 'PP-1' | 8.0 | 8.0 | 9.0 | 9.0 | 9.0 | 8.0 | 9.0 |
| 'Ecoturf' | 7.0 | 8.7 | 7.2 | 8.7 | 9.0 | 7.2 | 7.5 |
| 'Arblick' | 7.8 | 8.5 | 7.2 | 9.0 | 8.7 | 7.7 | 8.2 |
| 'Florigraze' | 4.5 | 4.2 | 4.7 | 6.7 | 6.5 | 3.5 | 6.0 |
| 'Arbrook' | 5.8 | 6.0 | 5.2 | 6.7 | 6.5 | 4.7 | 6.7 |
| LSD-5% | 1.1 | 1.0 | 1.0 | 0.5 | 0.9 | 0.7 | 0.8 |

[z]1 = less than 20% canopy coverage, 2 = 20 to 30% canopy coverage, 3 = 30 to 40% canopy coverage, 4 = 40 to 50% canopy coverage, 5 = 50 to 60% canopy coverage, 6 = 60 to 70% canopy coverage, 7 = 70 to 80% canopy coverage, 8 = 80 to 90% canopy coverage, 9 = 100% canopy coverage.

TABLE 7

Pepper spot ratings on five *Arachis glabrata* perennial peanut genotypes planted at Tifton, GA on 18 May 2006.

| | Disease - Pepper Spot[z] | | | |
|---|---|---|---|---|
| | 2008 | 2009 | | 2010 |
| Entry | Oct. 7 | Oct. 15 | Dec. 16 | Nov. 29 |
| 'PP-1' | 1.0 | 1.0 | 3.5 | 1.5 |
| 'Ecoturf' | 1.3 | 2.0 | 3.2 | 2.2 |
| 'Arblick' | 1.0 | 1.0 | 2.0 | 1.7 |
| 'Florigraze' | 1.5 | 6.0 | 5.7 | 4.2 |
| 'Arbrook' | 1.0 | 4.2 | 5.0 | 4.2 |
| LSD-5% | 0.4 | 1.3 | 1.0 | 2.0 |

[z]Pepper spot - 1 = no disease, 9 = high disease. Disease caused by *Leptosphaerulina crassiasca*.

TABLE 8

Leaf width on individual leaves of eight *Arachis glabrata* perennial peanut genotypes planted at Tifton, GA and Quincy, FL.

| | Leaf Width (mm) | | | | | |
|---|---|---|---|---|---|---|
| | Tifton, GA | | | | | Quincy, FL |
| | 2009 | | 2011 | 2012 | | 2010 |
| Entry | Jul. 30[z] | Aug. 31[y] | Jul. 25[x] | Jul. 25[z] | May 29[y] | Aug. 31[w] |
| 'PP-1' | 4.0 | 6.9 | 7.5 | 6.0 | 6.7 | 7.8 |
| 'Pointed Leaf' | | 10.0 | | | 8.5 | 8.4 |
| 'Ecoturf' | 10.0 | | | 11.0 | | |
| 'Arblick' | 10.0 | | | 11.0 | | |
| 'Florigraze' | 8.0 | | | 8.0 | | |
| 'Arbrook' | 11.0 | | | 10.0 | | |
| A42 | | | 8.8 | | | |
| LSD-0.05% | 1.0 | 0.5 | 1.2 | 1.0 | 0.9 | 0.6 |

[z]Planted 18 May 2006 at Tifton, GA. Four replications per entry. Six leaflets were measured per replication.
[y]Planted 14 Jun. 2011 at Tifton, GA. Seven replications per entry. Three leaflets were measured per replications.
[x]Planted 26 May 2010. Ten replications per entry. Three leaflets were measured per replication.
[w]Planted 10 Apr. 2009 Quincy, FL. Five replications per entry. Six leaflets were measured per replication.

TABLE 9

Leaf length on individual leaves of eight *Arachis glabrata* genotypes planted on 18 May 2006 and 2010 at Tifton, GA and Quincy, FL.

| | Leaf Length (mm) | | | | | |
|---|---|---|---|---|---|---|
| | Tifton, GA | | | | | Quincy, FL |
| | 2009 | | 2011 | 2012 | | 2010 |
| Entry | Jul. 30[z] | Aug. 31[y] | Jul. 25[x] | Jul. 25[z] | May 29[y] | Aug. 21[w] |
| 'PP-1' | 25.0 | 31.6 | 34.3 | 22.0 | 30.2 | 36.6 |
| 'Pointed Leaf' | | 27.5 | | | 27.8 | 35.5 |
| 'Ecoturf' | 26.0 | | | 18.0 | | |
| 'Arblick' | | | | 17.0 | | |
| 'Florigraze' | 28.0 | | | 18.0 | | |
| 'Arbrook' | 36.0 | | | 21.0 | | |
| A42 | | | 38.1 | | | |
| LSD-0.05% | 3.0 | 4.1 | 5.0 | 2.0 | 2.0 | 2.7 |

[z]Planted 18 May 2006 at Tifton, GA. Four replications per entry. Six leaflets were measured per replication.
[y]Planted 14 Jun. 2011 at Tifton, GA. Seven replications per entry. Three leaflets were measured per replications,
[x]Planted 26 May 2010. Ten replications per entry. Three leaflets were measured per replication.
[w]Planted 10 Apr. 2009 Quincy, FL. Five replications per entry. Six leaflets were measured per replication.

TABLE 10

Leaf area on individual leaves of eight *Arachis glabrata* genotypes planted at Tifton, GA and Quincy, FL.

| | Leaf Area ($cm^2$) | | | | | |
|---|---|---|---|---|---|---|
| | Tifton, GA | | | | | Quincy, FL |
| | 2009 | | 2011 | | 2012 | 2010 |
| Entry | Jul. 30[z] | Aug. 31[y] | Jul. 25 | Jul. 25[z] | May 29[y] | Aug. 21 |
| 'PP-1' | 3.0 | 4.6 | 5.2 | 4.0 | 4.2 | 5.1 |
| 'Pointed Leaf' | | 6.5 | | | 5.3 | 5.5 |
| 'Ecoturf' | 7.0 | | | 6.4 | | |
| 'Arblick' | 6.0 | | | 6.1 | | |

TABLE 10-continued

Leaf area on individual leaves of eight *Arachis glabrata* genotypes planted at Tifton, GA and Quincy, FL.

| | Leaf Area ($cm^2$) | | | | | |
|---|---|---|---|---|---|---|
| | Tifton, GA | | | | | Quincy, FL |
| | 2009 | | 2011 | | 2012 | 2010 |
| Entry | Jul. 30[z] | Aug. 31[y] | Jul. 25 | Jul. 25[z] | May 29[y] | Aug. 21 |
| 'Florigraze' | 6.0 | | | 4.7 | | |
| 'Arbrook' | 11.0 | | | 6.7 | | |
| A42 | | | 7.4 | | | |
| LSD-0.05% | 2.0 | 1.0 | 1.5 | 1.0 | 0.7 | 0.8 |

[z]Planted 18 May 2006 at Tifton, GA. Four replications per entry. Four leaves were measured per replication.

[y]Planted 14 Jun. 2011 at Tifton, GA. Seven replications per entry. Three leaves were measured per replications.

[x]Planted 26 May 2010. Ten replications per entry. Three leaves were measured per replication.

[w]Planted 10 Apr. 2009 Quincy, FL. Five replications per entry. Six leaves were measured per replication.

TABLE 11

Flower number ratings on six *Arachis glabrata* perennial peanut genotypes planted at Quincy, FL on 10 Apr. 2009.

| | Ratings for Number of Flowers[z] | | | | |
|---|---|---|---|---|---|
| | 2010 | | | 2011 | |
| Cultivar | 2 Feb. | 30 Jul. | 30 Jul.[y] | 1 Jun. | 1 Jun.[x] |
| 'PP-1' | 4.8 | 4.2 | 5.6 | 3.8 | 3.0 |
| 'Pointed Leaf' | 4.8 | 5.0 | 6.0 | 4.0 | 3.2 |
| 'EcoTurf' | 2.0 | 2.4 | 2.8 | 2.6 | 4.0 |
| 'Arblick' | 4.6 | 5.0 | 5.8 | 5.2 | 6.0 |
| 'Florigraze' | 3.8 | 3.4 | 3.6 | 2.8 | 2.8 |
| 'Arbrook' | 3.2 | 2.0 | 2.0 | 2.4 | 1.6 |
| LSD-5% | 0.7 | 0.9 | 0.8 | 1.5 | 1.4 |

[z]Rating for number of flowers on scale of 1 to 5 with 1 = none and 5 = many.

[y]After defoliation to six cm on 14 Jul., 2010.

[x]After defoliation to six cm on 12 May, 2011.

TABLE 12

Flower number ratings on six *Arachis glabrata* perennial peanut genotypes planted at Gainesville, FL on Jun. 28, 2010.

| | Flower Number[z] | | | | |
|---|---|---|---|---|---|
| | 2011 | | | | 2012 |
| Cultivar | 20 Apr. | 1 Jun. | 30 Sep. | 22 Oct. | 21 Mar. |
| 'PP-1' | 1.0 | 4.0 | 3.8 | 2.5 | 4.2 |
| 'Pointed Leaf' | 1.0 | 3.7 | 3.2 | 2.2 | 2.7 |
| 'Ecoturf' | 1.5 | 4.5 | 2.0 | 3.2 | 2.5 |
| 'Arblick' | 1.7 | 6.0 | 3.8 | 3.7 | 1.0 |
| 'Florigraze' | 2.5 | 5.2 | 2.2 | 4.2 | 2.7 |
| 'Arbrook' | 1.7 | 3.5 | 1.0 | 2.5 | 1.7 |
| LSD-5% | 0.8 | 2.0 | 0.9 | 0.7 | 1.2 |

[z]Flower number ratings on scale of 1 to 9 where 1 = no flowers and 9 = profuse flowering.

TABLE 13

Ratings for plant color on six *Arachis glabrata* perennial peanut genotypes planted at Gainesville, FL[z] and Quincy, FL[y].

| | Plant Color[x] | | | | | | |
|---|---|---|---|---|---|---|---|
| | Quincy 2010 | | | | Gainesville 2011 | | |
| Cultivar | 30 Jul. | 30 Jul.[w] | 27 Oct. | 27 Oct.[w] | 20 Apr. | 15 Jun. | 22 Oct. |
| 'PP-1' | 8.6 | 9.0 | 6.6 | 7.2 | 2.7 | 2.7 | 2.2 |
| 'Pointed Leaf' | 8.8 | 8.8 | 7.0 | 7.4 | 2.5 | 3.0 | 2.0 |
| 'Ecoturf' | 7.6 | 7.6 | 6.6 | 7.8 | 2.0 | 2.5 | 2.0 |
| 'Arblick' | 7.6 | 7.8 | 6.0 | 7.2 | 2.0 | 3.0 | 2.0 |
| 'Florigraze' | 6.4 | 6.4 | 5.0 | 6.4 | 2.0 | 1.2 | 2.0 |
| 'Arbrook' | 7.8 | 8.0 | 6.0 | 7.0 | 2.0 | 2.0 | 2.0 |
| LSD-5% | 0.6 | 0.9 | 1.0 | 0.8 | 0.5 | 0.6 | 0.3 |

[z]Planted Jun. 28, 2010.

[y]Planted Apr. 10, 2009.

[x]Plant color ratings on scale of 1 to 9 where 1 = brown and 9 = dark green.

[w]After defoliation to six cm on Jul. 14, 2010.

TABLE 14

Height measurements on six *Arachis glabrata* perennial peanut genotypes planted at Quincy, FL on Apr. 10, 2009.

| | Height (cm)[z] | | | | | |
|---|---|---|---|---|---|---|
| | 2010 | | | | 2011 | |
| Cultivar | 30 Jul. | 30 Jul.[y] | 27 Oct. | 27 Oct.[y] | 1 Jun. | 1 Jun.[x] |
| 'PP-1' | 16 | 10 | 14 | 9 | 14 | 9 |
| 'Pointed Leaf' | 11 | 9 | 13 | 8 | 11 | 10 |
| 'Ecoturf' | 35 | 17 | 27 | 18 | 29 | 13 |
| 'Arblick' | 15 | 13 | 15 | 13 | 14 | 6 |
| 'Florigraze' | 36 | 24 | 24 | 26 | 30 | 27 |
| 'Arbrook' | 39 | 38 | 30 | 39 | 43 | 43 |
| LSD-5% | 6 | 4 | 7 | 4 | 5 | 5 |

[z]Height measured from ground level to top of canopy.

[y]After defoliation to six cm on Jul. 14, 2010.

[w]After defoliation to six cm on May 12, 2011.

TABLE 15

Rating for canopy density on six *Arachis glabrata* perennial peanut genotypes planted at Quincy, FL on Apr. 10, 2009.

| | Canopy Density[z] | | | | |
|---|---|---|---|---|---|
| | 2010 | | | 2011 | |
| Cultivar | 30 Jul. | 30 Jul.[z] | 27 Oct. | 27 Oct.[y] | 1 Jun. |
| 'PP-1' | 7.2 | 7.2 | 4.0 | 4.0 | 8.6 |
| 'Pointed Leaf' | 6.4 | 7.0 | 3.2 | 4.0 | 8.4 |
| 'Ecoturf' | 7.4 | 8.4 | 7.4 | 8.4 | 8.8 |
| 'Arblick' | 7.6 | 7.8 | 7.2 | 8.0 | 9.0 |
| 'Florigraze' | 6.4 | 7.8 | 4.8 | 7.2 | 9.0 |
| 'Arbrook' | 5.6 | 6.2 | 5.2 | 6.4 | 8.6 |
| LSD-5% | 1.0 | 0.8 | 1.0 | 0.7 | 0.6 |

[z]Canopy density ratings on scale of 1 to 9 where 1 = bare ground and 9 = full canopy.

[y]After defoliation to six cm on Jul. 14, 2010.

TABLE 16

Ratings for spring green-up and freeze damage (on leaves) on six *Arachis glabrata* perennial peanut genotypes planted at Gainesville, FL[z] and Quincy, FL[y].

| | Spring Green-up[x] | Freeze Damage[w] | |
|---|---|---|---|
| Cultivar | Mar. 21, 2012 | Nov. 18, 2011 | Jan. 5, 2012 |
| 'PP-1' | 4.9 | 7.5 | 4.6 |
| 'Pointed Leaf' | 5.0 | 10.0 | 3.4 |
| 'Ecoturf' | 5.0 | 45.0 | 3.2 |
| 'Arbrick' | 5.0 | 51.2 | 3.0 |
| 'Florigraze' | 3.5 | 40.0 | 3.2 |
| 'Arbrook' | 4.7 | 25.5 | 3.6 |
| LSD-5% | 0.5 | 34.9 | 0.6 |

[z]Planted Jun. 28, 2010.

[y]Planted Apr. 10, 2009.

[x]Spring green-up at Gainesville, FL rated on a scale of 1 to 5 where 1 = brown and 5 = completely green.

[w]Freeze damage to leaves at Gainesville, FL on Nov. 18, 2011 rated as percent leaf damage after −2° C. for two days. Freeze damage ratings on leaves on scale of 1 to 5 at Quincy, FL on Jan. 5, 2012 where 1 = severe damage and 5 = tolerant. Rated two days after −8° C. for two days.

TABLE 17

Leaf scorch and leaf spot ratings on six *Arachis glabrata* perennial peanut genotypes planted at Quincy, FL on Apr. 10, 2009.

| | Leaf Scorch[z] | | | | |
|---|---|---|---|---|---|
| | 2010 | | 2011 | | 2012 |
| Cultivar | 15 Jul. | 27 Oct. | 1 Jun. | 20 Oct. | 1 Jun. |
| 'PP-1' | 4.2 | 3.0 | 3.4 | 3.4 | 3.6 |
| 'Pointed Leaf' | 4.4 | 2.8 | 3.0 | 3.6 | 3.4 |
| 'Ecoturf' | 1.4 | 1.0 | 1.0 | 1.0 | 1.0 |
| 'Arblick' | 1.0 | 1.0 | 1.0 | 1.0 | 1.0 |
| 'Florigraze' | 1.2 | 1.6 | 1.0 | 2.2 | 2.0 |
| 'Arbrook' | 1.0 | 1.0 | 1.0 | 1.0 | 1.0 |
| LSD-5% | 0.6 | 0.4 | 0.7 | 0.4 | 0.4 |

| | Leaf Spot[z] | | | | |
|---|---|---|---|---|---|
| | 2010 | | 2011 | | 2012 |
| Cultivar | 15 Jul. | 27 Oct. | 1 Jun. | 10 Oct. | 1 Jun. |
| 'PP-1' | 1.0 | 1.0 | 1.0 | 1.0 | 1.0 |
| 'Pointed Leaf' | 1.0 | 1.0 | 1.0 | 1.0 | 1.0 |
| 'Ecoturf' | 1.0 | 1.0 | 1.0 | 1.0 | 1.0 |
| 'Arblick' | 1.0 | 1.0 | 1.0 | 1.0 | 1.0 |
| 'Florigraze' | 8.4 | 6.6 | 7.4 | 7.2 | 6.2 |
| 'Arbrook' | 2.6 | 2.2 | 2.2 | 2.0 | 2.0 |
| LSD-5% | 0.4 | 0.4 | 0.4 | 0.5 | 0.2 |

[z]Pepper spot and leaf scorch ratings on scale of 1 = no disease, 5-severe lesions and 9 = leaf drop.
Both diseases caused by *Leptosphaerulina crassiasca*.

TABLE 18

Means (25 measurements) for morphological characteristics of PP-1 perennial peanut.

| Morphological | Measurements | | | Standard |
|---|---|---|---|---|
| Characteristics | Minimum | Maximum | Mean | Error |
| Flower Height | 12 | 17 | 15.3 | 1.5 |
| Petiole Length | 7 | 14 | 10.9 | 1.4 |
| Petiole Width | 0.49 | 1.11 | 0.8 | 0.2 |
| Petal Length | 15 | 21 | 18.5 | 1.9 |
| Petal Width | 16 | 23 | 21.1 | 1.6 |
| Sepal Length | 6 | 8 | 7.2 | 0.6 |
| Sepal Width | 3 | 5 | 4.3 | 0.6 |

TABLE 18-continued

Means (25 measurements) for morphological characteristics of PP-1 perennial peanut.

| Morphological | Measurements | | | Standard |
|---|---|---|---|---|
| Characteristics | Minimum | Maximum | Mean | Error |
| Internode Length | 9 | 22 | 14.2 | 3.1 |
| Internode Width | 1.3 | 2.9 | 1.9 | 0.3 |

In summary, 'PP-1' is a dark-green, narrow-leafed plant that produces an abundance of yellow orange flowers in the spring, summer and fall. It has performed as well or better in Georgia and Florida than most released cultivars. It has performed well in Poteet, Tex. and Lake City, Fla., in non-replicated tests and in yards at Brian Schwartz's and Wayne Hanna's homes for two to six years. 'PP-1' produces a low-maintenance, low-input, ornamental, and colorful ground cover. Preliminary studies show that it can be used in combination with lawn grasses to furnish nitrogen for the grass.

BRIEF DESCRIPTION OF THE FIGURES

The accompanying colored photographs illustrate the overall appearance and distinct characteristics of the new cultivar of *A. glabrata*, 'PP-1'. The colors in the photographs are as close as possible with the photographic and printing technology utilized.

BOTANICAL DESCRIPTION

Figure 1:
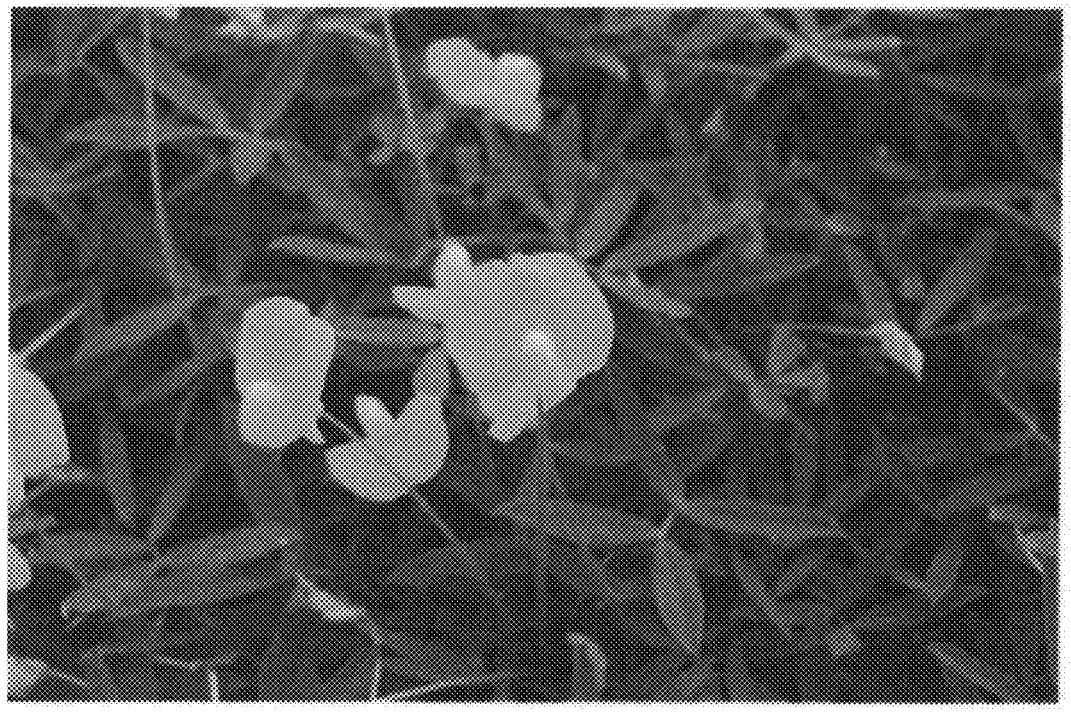
FIG. 1 is a closeup photograph of flowers and leaves of the new cultivar 'PP-1'.
Figure 2:
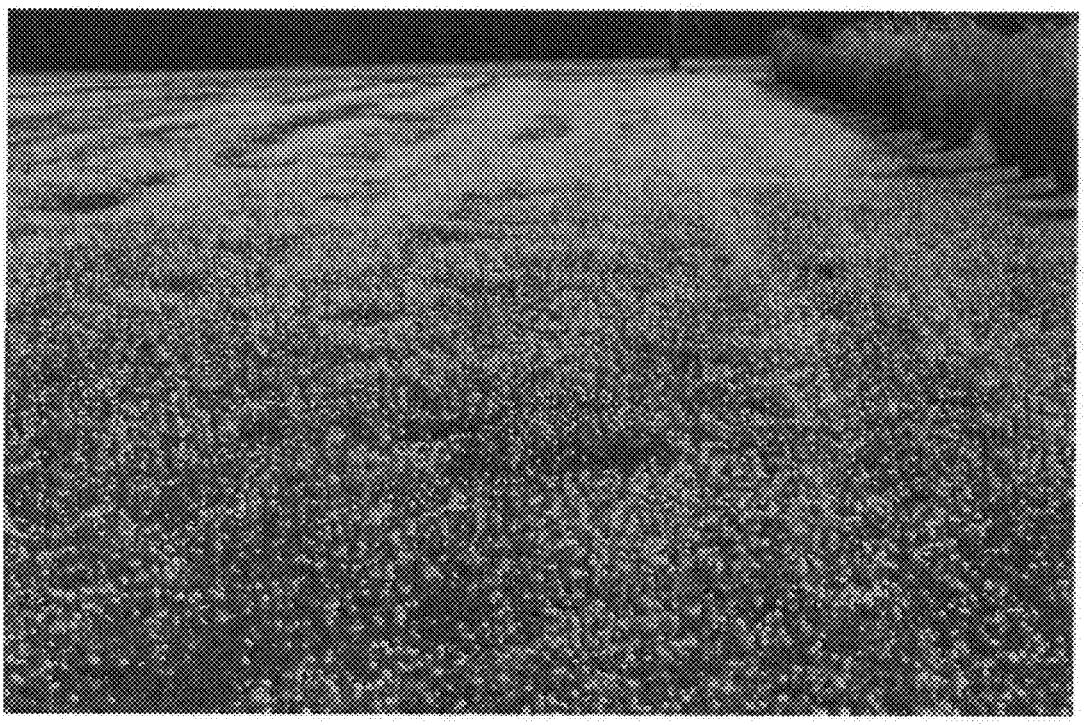
FIG. 2 is a photograph of plants of the new cultivar 'PP-1'.

'PP-1' is a perennial, vegetatively propagated dark-green narrow-leaf perennial peanut recommended for use as an ornamental in USDA zones 8b and 9. It has survived in a 2006 replicated test at Tifton from 2006 to 2012 (when the test was destroyed). It has survived under no management next to perennial peanut research plot area since 1954. All data are from plants established as single stem propagules in mid-May, and rated throughout the years. The term "standard" in the description below refers to typical properties of the observed plant.

Plant:

*Mature plant height*.—Approximately 6-20 cm.

*Plant diameter* (*at* 123 *days*).—Approximately 89-93 cm.

*Leaflet width*.—Approximately 4-8 mm.

*Leaflet length*.—Approximately 27-32 mm.

*Leaflet shape*.—Narrow, elliptic.

*Leaflet apex*.—Acute.

*Leaflet base*.—Rounded.

*Leaflet margin*.—Entire.

*Adaxial leaflet venation color*.—About Green RHS 144A.

*Abaxial leaflet venation color*.—About Green RHS 138D.

*Petiole length*.—About 7-14 cm.

*Petiole diameter*.—About 0.49-1.11 mm.

*Petiole color*.—Red-Purple group RHS 62B.

*Adaxial leaflet color*.—About Green RHS 144A.

*Abaxial leaflet color*.—About Green RHS 144A.

*Flower height*.—About 12-17 cm.
*Bloom time*.—About April through September in U.S.; winter hardiness zone 8.
*Petal number per flower*.—Five.
*Standard petal length*.—About 15-21 mm.
*Standard petal width*.—About 16-23 mm.
*Flower diameter*.—About 16-23 mm (same as standard petal width).
*Standard petal shape*.—Papilionaeeous, two-lobed.
*Standard petal apex*.—Retuse.
*Standard petal margin*.—Entire.
*Standard petal flower color*.—Standard upper petal surface transitions from Orange Group RHS 24A in the center to Yellow-Orange Group RHS 14C toward the margins. Standard lower petal surface Yellow-Orange Group RHS 24C.
*Wing petal flower color*.—Yellow-Orange Group 14D.
*Sepal number*.—Two.
*Sepal* (*large*) *length*.—About 6-8 mm.
*Sepal* (*large*) *width*.—About 3-5 mm.
*Sepal* (*large*) *shape*.—Acuminate.
*Sepal* (*small*) *shape*.—Acicular.
*Sepal* (*large*) *margin*.—Entire.
*Sepal* (*large*) *base*.—Round with few trichomes.
*Sepal* (*large*) *apex*.—One large with four subulate teeth, and one small tooth.
*Adaxial sepal color*.—About Greyed-white group RHS 156B.
*Abaxial sepal color*.—About Greyed-white group RHS 156D.
*Anther number per flower*.—Eight, four are spherical and four are elongated.
*Internode length*.—About 9-22 mm.
*Internode width* (*stem diameter*).—About 1.3-2.9 mm.
*Internode* (*stem*) *color* (*facing ground*).—About Green group RHS 139C.
*Internode* (*stem*) *color* (*facing sun*).—About Red-purple RHS 59A.
*Stem* (*runner length*).—Growth after 123 days was mean equals 51.7 cm with a standard of error of 7.2.
*Number nuts produced*.—Extremely rare; single seeded pods; less than 11 mm long and 6 mm wide.
*Cucumvorus peanut stunt virus*.—None.

What is claimed is:

1. A new and distinct cultivar of *Arachis glabrata* plant named 'PP-1' substantially as illustrated and described herein.

* * * * *